| United States Patent [19] | [11] Patent Number: 4,462,986 |
| Smith | [45] Date of Patent: Jul. 31, 1984 |

[54] SYNERGISTIC ANTI-HERPES COMPOSITIONS

[75] Inventor: Kendall O. Smith, San Antonio, Tex.

[73] Assignee: Ens Bio Logicals, Inc., Ottawa, Canada

[21] Appl. No.: 439,121

[22] Filed: Nov. 4, 1982

[51] Int. Cl.³ .................. A61K 45/02; A61K 31/505; A61K 31/525

[52] U.S. Cl. ..................................... 424/85; 424/251; 424/253

[58] Field of Search .......................... 424/85, 251, 253

[56] References Cited

U.S. PATENT DOCUMENTS 4,060,616 11/1977 Schaeffer ............................ 544/276
4,347,360 8/1982 Ogilvie ................................ 424/251

OTHER PUBLICATIONS

Scott, G., et al., British Medical Journal, pp. 1558–1562, Jun. 28, 1980.
Borzov, M., et al., Vestnik Dermatologii i Venerologii, vol. 45, No. 9, pp. 14–17, 1971.

*Primary Examiner*—Blondel Hazel
*Attorney, Agent, or Firm*—Murray, Whisenhunt & Ferguson

[57] ABSTRACT

Combinations of 9-[[2-hydroxy-1-(hydroxymethyl)-ethoxy]methyl]guanine or a pharmaceutically acceptable salt thereof, and interferon show synergy in their activity against herpes virus infections.

8 Claims, No Drawings

SYNERGISTIC ANTI-HERPES COMPOSITIONS

FIELD OF THE INVENTION

This invention relates to pharmaceutical compositions, and more particularly to pharmaceutical compositions useful for treatment of viral infections such as herpes infections in mammals.

BACKGROUND OF THE INVENTION

Herpes simplex virus (HSV) infections are widespread in human populations, and pose a particularly difficult health problem. Genital herpes poses a serious health threat to women, in particular. Pregnant women with active genital herpes infections at the time of delivery have a 50—50 chance of passing it on to their babies. The American Academy of Pediatrics states that 60% of those babies born with HSV infections will die, and half of the survivors will suffer severe damage to the brain, nervous system and eyes ("Pediatrics" 66, 147–9, 1980). It has also been proposed that HSV2 may have a role in the onset of cervical cancer. There has been observed an association between sexual intercourse and cervical cancer, which may be explained by transmission of HSV-2.

Unlike other sexually transmitted diseases such as gonorrhea, syphilis and nongonococcal urethritis, there is currently no cure for herpes infections. Many of the drugs currently in clinical use may not be effective in reducing the severity or the duration of the symptoms. Even after the symptoms disappear, herpes virus tends to remain dormant in nerve tissue, only to be reactivated at a later date to an active phase of infection, causing lesions ("cold sores") and other symptoms to recur. A drug can be considered effective if it diminishes the severity of the lesions, allows for more rapid healing, extends the period between recurrences of herpes infections or stops recurrences altogether.

Herpes simplex virus is one member of the family "Herpetoviridae"; other members of this family which infect humans are varicella-zoster, cytomegalovirus and Epstein-Barr virus. The family also includes various members which attack animals. For example, there are three types of equine herpesvirus, a swine herpesvirus, a canine herpesvirus and a feline herpesvirus, among others.

As with all viruses, herpes virus invades healthy host cells on which it relies to provide its needs for replication. Herpes viruses code for some of the enzymes they need for replication, instead of relying completely on the host cell for all their needs. Hence, herpes viruses are subject to selective inhibition by certain drugs that interfere specifically with viral enzymes.

BRIEF REFERENCE TO THE PRIOR ART

A variety of drugs have been proposed and tested for treatment of HSV infections. For example, U.S. Pat. No. 4,199,574 Schaeffer, issued Apr. 22, 1980 discloses a wide variety of compounds said to be useful in such treatments, extensive testing of one of which (acycloguanosine or acyclovir, 9-[2-hydroxyethoxymethyl]-guanine) has been reported in the literature, with sometimes promising results. Another drug which has been explored is 5-iododeoxyuridine (IDU), but this has been reported to be effective only against herpes infections of the eyes. It also has undesirable side effects, associated with toxicity to normal cells. Adenine arabinoside (ara-A), phosphonoformic acid (PFA), phosphonoacetic acid (PAA), 2-deoxy-D-glucose (2DG), and 5-(2-halogenovinyl)-2′-deoxyuridines as exemplified by bormovinyl-deoxyuridine (BVDU) and its iodo-analog are other drugs which have some demonstrated activity against human herpesviruses.

U.S. Pat. No. 3,767,795 Schleicher et al, assigned to Abbott Laboratories, describes a method of preventing or treating herpesvirus infections in animals by administering phosphonoacetic acid or its salts.

U.S. Pat. No. 4,215,113 Eriksson et al, assigned to Astra Lakemedel AB, describes a method of treating virus infections, including herpesvirus, by administering phosphonoformic acid or its salts to infected animals.

U.S. patent application Ser. No. 302,790 Ogilvie, filed Sept. 16, 1981, describes 9-[[2-hydroxy-1-(hydroxymethyl)-ethoxy]methyl]guanine and its activity against herpes virus.

Patent Co-operation Treaty Application US82/00/182 K. O. Smith and ens Bio Logicals inc., describes synergistic mixtures of 9-[[2-hydroxy-1-(hydroxymethyl)-ethoxy]methyl]guanine and PFA or PAA or salts thereof, for use in treatment of herpes virus infected cells.

SUMMARY OF THE INVENTION

It has now been found that therapeutic compositions having good activity against herpes virus can be prepared from combinations of interferon and 9-[[(2-hydroxy-1-(hydroxymethyl)-ethoxy]methyl] guanine, or a pharmaceutically acceptable salt thereof. These combinations are much more effective than one could have predicted from a consideration of the activities of the compounds individually, indicating that some form of synergistic effect is taking place.

Thus, according to the present invention, there is provided a therapeutic composition having activity against herpes virus infections and comprising in combination at least one interferon compound in admixture with 9-[[2-hydroxy-1-(hydroxymethyl)-ethoxy]methyl] guanine, or a pharmaceutically acceptable salt thereof.

DESCRIPTION OF THE PREFERRED EMBODIMENTS

Interferon is a low molecular weight polypeptide produced as an excretion from various types of viable mammalian cells. Its properties, chemical nature and methods of preparation and recovery have been extensively studied and documented in recent years, because of its potentially valuable pharmacological properties. It is known to exist in several types. Whilst all types of interferon are useful in composition of the present invention, it is preferred to use interferon-$\alpha$. Interferon concentrations are commonly expressed as standard "units" which are internationally accepted and documented, and relate to the potency of a given quantity of interferon to inhibit a virus replication under standard conditions. 9-[[2-hydroxy-1-(hydroxymethyl)-ethoxy]-methyl] guanine, (hereinafter sometimes referred to a G*) and its processes for preparation are described in aforementioned U.S. application Ser. No. 302,790 Ogilvie.

The compositions of the invention may of course include more than two active ingredients. G* may be present as the free base, or alternatively as a pharmaceutically acceptable salt such as hydrochloride.

The preferred compositions of the present invention appear to be active against a wide representative variety of strains of HSV, both types I and II. The compositions may also be active against equine herpesvirus of various types, and swine herpesvirus (pseudorabies virus).

Nearly every HSV strain produces virus particles which are partially resistant to each of the drugs mentioned above. For example, if one examines a typical titration curve which shows the effect of varying drug concentrations upon HSV plaque formations (the viral plaque titration method of Roizman and Roane referred to in more detail below), the curve is sigmoid, i.e. there are a few viral plaques which emerge in the presence of drug concentration which readily suppresses other plaques. It is these partially drug-resistant virus plaques which can sometimes be suppressed by a second drug possible having a mode of action different from the first drug. The result may be synergistic action between the first and second drugs, as set out below.

The relative amounts of the drugs in the compositions according to the invention can be varied over wide limits. The optimum amount of each drug varies according to the nature of the formulation in which the drugs are to be applied, the type and strain of HSV to be treated, and the severity and location of the infection, among other factors. The amount of interferon, as noted above, is commonly expressed in standard units. Generally, compositions containing from about 50-500,000 units interferon per microgram of G* are effective. Preferred compositions are those containing from about 1,000-200,000 units of interferon per microgram of G*.

For administration to patients, the compositions of the invention may be applied topically as ointment, cream or powder, parenterally, interthecally, as nose drops, eye drops or as an aerosol for inhalation, again depending upon the nature and location of the infection to be treated. Effective unit doses for administration of the compositions interthecally or parenterally are suitably in the range from about 0.1-100 mg of total drugs in the chosen combinations, per kg mammal body weight, most suitably in the 0.5-20 mg per kg and most preferably about 5 mg per kg, on the basis of a dosage administered from 2-4 times daily. It is preferred to treat the infection with relatively large doses of the combination of drugs at the outset, so as to limit the chances of development of resistant viral strains in the infection.

For topical administration, ointments or creams in conventional inert bases (e.g. petrolatum, etc.) can be formulated, in the known way. An amount from about 0.1-10 weight percent of total drugs, preferably from about 0.5-5 weight percent of total drugs, provides a suitable concentration in an ointment or cream, for topical administration 1-4 times per day. Such topically applied formulations are effectively holding a reservoir of the active drugs against the infected site, so that the concentrations of drugs in the formulations are not critical, provided of course that a dosage level harmful to surrounding skin areas is not used.

DETAILED DESCRIPTION OF SPECIFIC PREFERRED EMBODIMENTS

The invention is further illustrated in the following specific experimental results and examples.

EXAMPLE 1

Human fetal fibroblasts (HFF) derived from fetal tissues were used in these experiments. Cells were grown and maintained in Basal Medium Eagle (BME) supplemented with 0.112% sodium bicarbonate, 2 mML-glutamine, 2 mg% Neomycin and 20% (vol/vol) calf serum.

HSV-1-Patton strains, an old established, well-known strain of herpes simplex type 1 virus was used in the tests, as set out in the Tables presented below.

A viral plaque titration method (Roizman and Roane, 1961) was used to determine the titer of the HSV strain. Tissue culture dishes (35 by 10 mm, Corning) were seeded with cells and used for assays when they were approximately 75% monolayer. Volumes (0.2 ml) of logarithmic dilutions of the virus strain were inoculated onto each of two tissue culture dishes and adsorbed for 1 hr with intermittent shaking, the inoculum was removed and 2 ml of 20% BME containing 0.5% human immune serum globulin was added. After a 48 hr. incubation period at 36° C. in a 5% $CO_2$ atmosphere, the overlay medium was removed, and the cell sheets were stained with a 0.05% aqueous crystal violet solution. The plaque numbers were counted with the aid of a Nikon profile projector which magnified the dishes 10X. Duplicate results were averaged, and the number of plaque-forming units (PFU) was calculated. The virus titre is thus expressed as a number of plaque forming units to be seen after growth under these conditions.

As antiviral drugs in these experiments, there were used combinations of G* and interferon-$\gamma$ and $\alpha$.

In order to make comparisons between the activities of the various drugs and combinations, experiments were conducted by plaque titration to observe the antiviral potency, by observing and counting the number of PFUs per dish after growth of the infected cells in culture medium. For this purpose, tissue culture dishes (35 by 10 mm) with HFF cell monolayers at 75% confluence were inoculated with approximately 50 plaque-forming units of virus per 0.2 ml, and the virus was allowed to adsorb for 1 hr with intermittent shaking. After removal of the inoculum, 2 ml of 20% BME with 0.5% immune globulin and threefold dilutions of the appropriate drug were added to duplicate dishes. One set of dishes received no drug. After a 48 hr incubation period at 36° C. in a 5% $CO_2$ atmosphere, the overlay medium was removed, the cells were stained as described above, and plaques were counted. The counts of duplicate plates were averaged.

Combinations of the drugs were tested for activity by viral plaque titration, at various concentrations, and the drugs were individually plaque titrated for comparison purposes.

The results are given in the following Table. The virus titer results are expressed in plaque-forming units (PFU) per dish and, of course, the lower the figure the greater the inhibitory, anti-viral effect of the tested drug.

TABLE 1

Plaque Inhibition Tests against HSV-1-Patton Infected HFF cells

| | Interferon-$\gamma$ concentration (units per ml) | | | |
|---|---|---|---|---|
| | 10 PFU per dish | 100 PFU per dish | 1000 PFU per dish | 0 PFU per dish |
| G* concentration (micrograms per ml) 0.02 | 27 | 23 | 24 | 31 |
| 0.064 | 24 | 26 | 19 | 29 |
| 0.2 | 18 | 20 | 7 | 18 |
| 0.64 | 1 | 0 | 0 | 1 |
| 2.0 | 0 | 0 | 0 | 0 |
| 0 | 30 | 24 | 24 | 36 |

These figures show that, whilst interferon-γ alone has only slight effect on the virally infected cells and G* has effect at relatively high concentration, the combination in suitable proportions is much more effective, and permits the amount of compound G* to be reduced very significantly.

EXAMPLE 2

The procedures of Example 1 were essentially repeated, but using mixtures of equal proportion of interferon-γ and interferon-α, with various amounts of G*, and again using HFF cells infected with HSV-1-Patton. In each experiment, the amount of interferon was 1000 units per ml of interferon-γ and 1000 units per ml of interferon-α, for a total amount of 2000 units per ml of interferon. The virus titer results, in this case, are expressed as plaque forming units per ml, $\times 10^5$. The figure for "Fold Titer Reduction" is the ratio of the virus titer for the control, i.e. no drug, to that of the drug-present experiment. The results are presented in Table 2 below.

TABLE 2

| G* Concentration, micrograms/ml | With interferon | | No interferon | |
| --- | --- | --- | --- | --- |
| | PFU/ml $\times 10^5$ | Fold titre reduction | PFU/ml $\times 10^5$ | Fold titre reduction |
| 0.02 | 30 | 4.0 | 115 | 1.0 |
| 0.064 | 5 | 24.0 | 90 | 1.3 |
| 0 | 100 | 1.2 | 120 | 1.0 |

The results show that synergistic action occurs in these combinations of drugs, against the tested HSV strains. At least the same degree of synergy is to be expected in vivo.

EXAMPLE 3

In a further experiment, similarly virally infected HFF cells were incubated as described, and plaque titrated with various combinations of G* and an interferon-γ/interferon-α combination. In one set of dishes, no G* was used, and in the other set of dishes 0.05 micrograms per ml of G* was used. The interferon was in each case a mixture of equal amounts of interferon-γ and interferon-α, the numbers shown in the following results being the individual amounts of each component in the mixture.

The results are shown in Table 3. The figures are presented as "fold titre reduction", with the dishes containing no drugs being assigned the value of unity.

TABLE 3

| | Interferon Concentration (units/ml) | | | |
| --- | --- | --- | --- | --- |
| | 0 | 10 | 100 | 1000 |
| Fold titre reduction with 0 micrograms/ml G* | 1.0 | 1.1 | 1.1 | 1.6 |
| Fold titre reduction with 0.05 micrograms/ml G* | 1.0 | 1.3 | 3.0 | >27 |

The relative amounts and concentrations of drugs used in these examples are appropriate for in vitro testing and to demonstrate the synergy of the combinations, but are illustrative only. Relative amounts in combinations for in vivo use and in practical administration for HSV treatments are as discussed previously, and may not bear close relationship to the proportions shown in the specific examples herein.

I claim:

1. A therapeutic composition having activity against herpes simplex virus types HSV I and HSV II and comprising an effective amount of a composition comprising, in combination, at least one interferon compound in admixture with 9-[[2-hydroxy-1-(hydroxymethyl)-ethoxy]methyl] guanine or a pharmaceutically acceptable salt thereof, the relative amount of interferon therein being from about 50 to about 500,000 units per microgram of 9-[[2-hydroxyl-1-(hydroxymethyl)ethoxy]methyl] guanine or salt thereof.

2. The composition of claim 1 wherein the interferon is interferon-γ, interferon-α, or a mixture thereof.

3. The composition of claim 2, wherein the relative amount of interferon therein is from about 5000 to about 100,000 units per microgram of 9-[[2-hydroxy-1-(hydroxymethyl)ethoxy]methyl] guanine or salt thereof.

4. A process for treatment of herpes simplex virus types HSV I and HSV II infections in mammals which comprises administering thereto an effective amount of a therapeutic composition according to claim 1.

5. A process for the treatment of herpes simplex virus types HSV I and HSV II infections in mammals which comprises administering thereto an effective amount of a therapeutic composition according to claim 2.

6. A process for the treatment of herpes simplex virus types HSV I and HSV II infections in mammals which comprises administering thereto an effective amount of a therapeutic composition according to claim 3.

7. The composition of claim 2, wherein the relative amount of interferon therein is from about 5,000 to about 40,000 units per microgram of 9-[[2-hydroxy-1-(hydroxymethyl)ethoxy]methyl] guanine or salt thereof.

8. A process for the treatment of herpes simplx virus types HSV I and HSV II infections in mammals which comprises administering thereto an effective amount of a therapeutic composition according to claim 7.

* * * * *